US010130285B1

United States Patent
Singamsetty et al.

(10) Patent No.: US 10,130,285 B1
(45) Date of Patent: Nov. 20, 2018

(54) WEARABLE APPARATUS FOR PATIENT TRACKING

(71) Applicant: WiSilica Inc., Laguna Hills, CA (US)

(72) Inventors: Suresh Kumar Singamsetty, Aliso Viejo, CA (US); Dennis Ching Chung Kwan, San Diego, CA (US)

(73) Assignee: WiSilica Inc, Laguna Hills, CA (US)

( * ) Notice: Subject to any disclaimer, the term of this patent is extended or adjusted under 35 U.S.C. 154(b) by 0 days.

(21) Appl. No.: 15/713,662

(22) Filed: Sep. 24, 2017

(51) Int. Cl.
*A61B 5/11* (2006.01)
*H04W 4/80* (2018.01)
*A61B 5/00* (2006.01)
*G08B 21/22* (2006.01)
*G16H 10/60* (2018.01)

(52) U.S. Cl.
CPC ............. *A61B 5/1113* (2013.01); *H04W 4/80* (2018.02); *A61B 5/681* (2013.01); *G08B 21/22* (2013.01); *G16H 10/60* (2018.01)

(58) Field of Classification Search
CPC ........ A61B 5/1113; A61B 5/681; H04W 4/80; G16H 10/60; G08B 21/22
USPC .................................................... 340/539.11
See application file for complete search history.

(56) References Cited

U.S. PATENT DOCUMENTS

| | | | | |
|---|---|---|---|---|
| 3,715,570 A | * | 2/1973 | Weichselbaum | A61B 5/117 235/449 |
| 4,226,036 A | * | 10/1980 | Krug | G09F 3/005 24/16 PB |
| 8,410,926 B1 | * | 4/2013 | Gary, Jr. | A61B 5/002 340/539.12 |
| 2005/0108912 A1 | * | 5/2005 | Bekker | G09F 3/005 40/633 |
| 2007/0035401 A1 | * | 2/2007 | Bartz | G06K 19/041 340/572.8 |
| 2007/0275356 A1 | * | 11/2007 | Murphy | G09B 1/28 434/99 |
| 2011/0030256 A1 | * | 2/2011 | Juliano | G09F 3/005 40/633 |
| 2012/0016793 A1 | * | 1/2012 | Peters | G06Q 20/10 705/39 |
| 2012/0056719 A1 | * | 3/2012 | Krishna | G06K 19/07762 340/10.1 |
| 2013/0182382 A1 | * | 7/2013 | Vardi | G08B 13/1463 361/679.01 |
| 2015/0077257 A1 | * | 3/2015 | Pokrajac | G08B 13/06 340/572.8 |
| 2016/0104355 A1 | * | 4/2016 | Alexander | G08B 25/009 340/692 |
| 2017/0014035 A1 | * | 1/2017 | Newberry | A61B 5/02055 |
| 2017/0231494 A1 | * | 8/2017 | Pekander | A61B 5/0015 340/870.07 |

* cited by examiner

*Primary Examiner* — Kerri L McNally
(74) *Attorney, Agent, or Firm* — FSP LLC

(57) ABSTRACT

An apparatus for tracking patients utilizes a wristband with integrated radio frequency circuits (RFIC). The wristband may further incorporate an antenna on a flex PCB. The wristband may also be disposable and comprising means for replacing the RFIC.

12 Claims, 7 Drawing Sheets

WEARABLE APPARATUS FOR PATIENT TRACKING

CROSS-REFERENCE TO RELATED APPLICATIONS

This present disclosure claims the benefit of U.S. Provisional Application Ser. No. 62/421,610, filed on Nov. 14, 2016.

BACKGROUND

Patient tracking is a critically important task for hospitals and medical facilities. Knowing information about a patient and being able to locate that patient within a facility can mean the difference between life and death.

Currently, most patient tracking devices are bulky, expensive and impractical to use. Batteries must be recharged or replaced by hospital staff and the entire device must be re-used each time. This can lead to issues regarding the sterileness of the device which can be of particular concern for newborns and patients with suppressed immune systems. Additionally, tracking devices need to be able to notify nursing staff if the device is tampered with or removed.

Tracking devices also need to be energy efficient, because an increase in energy usage requires larger batteries and can lead to a need for frequent charging or battery changing during the patient's stay at the hospital. Given that some hospitals see a very large number of patients, it is also important that tracking devices be relatively inexpensive and easily replaceable. A high-cost for the construction or use of the devices may make it cost-prohibitive for hospitals to implement.

There is therefore a current need for an energy and cost-efficient patient tracking device that can be easily implemented by hospitals and medical facilities.

BRIEF SUMMARY OF THE INVENTION

The present invention solves the aforementioned problems by implementing a system and apparatus for tracking patients utilizing a wristband with a wireless transceiver that is able to communicate with a wireless network. The wristband may further incorporate an antenna on a flex PCB to allow for the band to be wrapped and fastened around a patients limbs. The wristband may also be disposable by comprising means for replacing the RFIC.

BRIEF DESCRIPTION OF DRAWINGS

To easily identify the discussion of any particular element or act, the most significant digit or digits in a reference number refer to the figure number in which that element is first introduced.

DETAILED DESCRIPTION

Overview

Herein various embodiments of a patient tracking tag and system and method(s) of operating the tracking tag and system are disclosed. These embodiments may be operated within a mesh network environment using various wireless protocols and technologies, including those defined below.

Mesh Network

A mesh network is a type of machine communication system in which each client node (sender and receiver of data messages) of the network also relays data for the network. All client nodes cooperate in the distribution of data in the network. Mesh networks may in some cases also include designated router and gateway nodes (e.g., nodes that connect to an external network such as the Internet) that are or are not also client nodes. The nodes are often laptops, cell phones, or other wireless devices. The coverage area of the nodes working together as a mesh network is sometimes called a mesh cloud.

Mesh networks can relay messages using either a flooding technique or a routing technique. Flooding is a routing algorithm in which every incoming packet, unless addressed to the receiving node itself, is forwarded through every outgoing link of the receiving node, except the one it arrived on. With routing, the message is propagated through the network by hopping from node to node until it reaches its destination. To ensure that all its paths remain available, a mesh network may allow for continuous connections and may reconfigure itself around broken paths. In mesh networks there is often more than one path between a source and a destination node in the network. A mobile ad hoc network (MANET) is usually a type of mesh network. MANETs also allow the client nodes to be mobile.

A wireless mesh network (WMN) is a mesh network of radio nodes. Wireless mesh networks can self-form and self-heal and can be implemented with various wireless technologies and need not be restricted to any one technology or protocol. Each device in a mobile wireless mesh network is free to move, and will therefore change its routing links among the mesh nodes accordingly.

Mesh networks may be decentralized (with no central server) or centrally managed (with a central server). Both types may be reliable and resilient, as each node needs only transmit as far as the next node. Nodes act as routers to transmit data from nearby nodes to peers that are too far away to reach in a single hop, resulting in a network that can span larger distances. The topology of a mesh network is also reliable, as each node is connected to several other nodes. If one node drops out of the network, due to hardware failure or moving out of wireless range, its neighbors can quickly identify alternate routes using a routing protocol.

Wearable Tag

Figure 1:
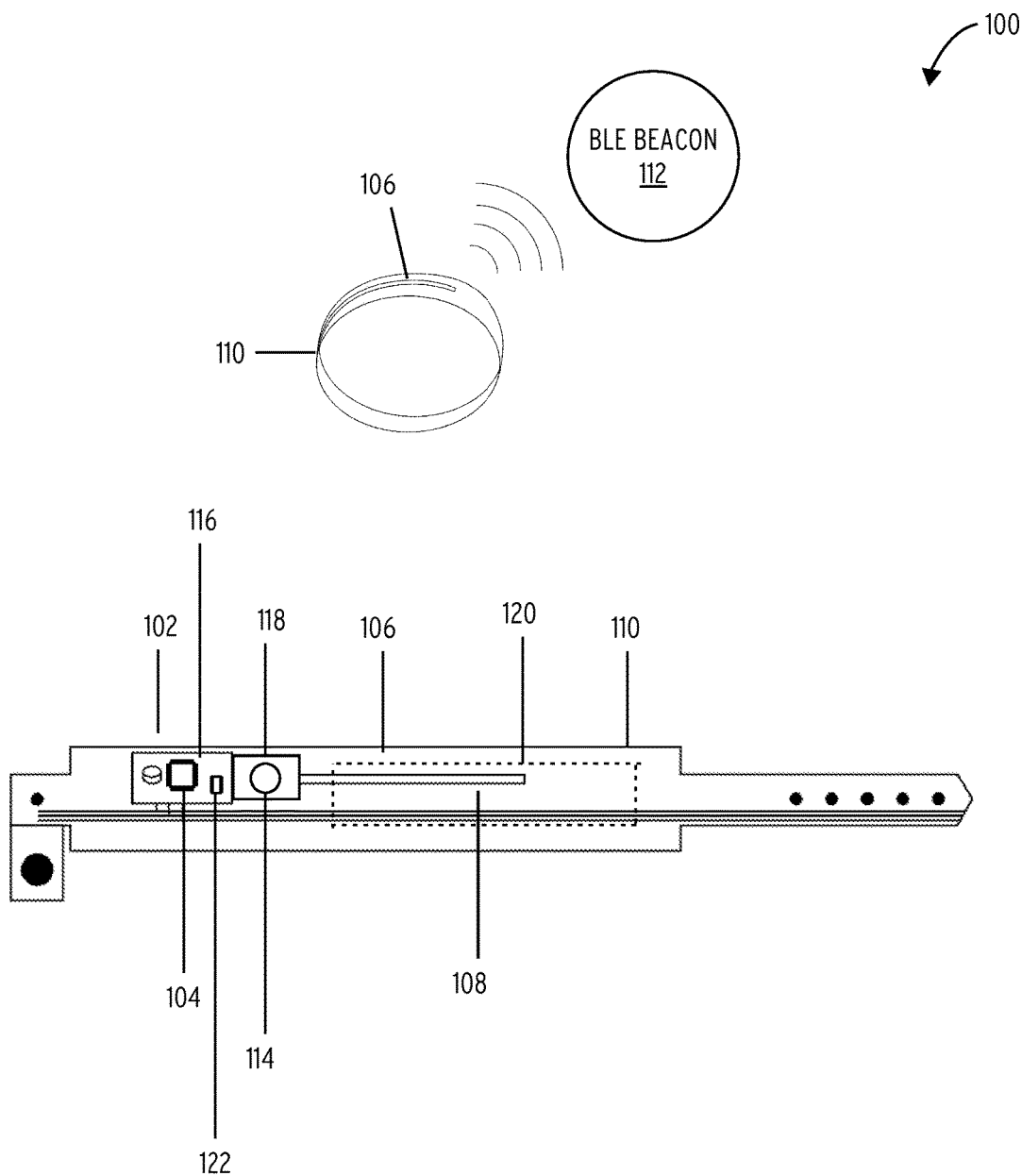
FIG. 1 illustrates an embodiment of a wearable apparatus for patient tracking 100.

FIG. 1 illustrates an embodiment of a wearable apparatus for patient tracking 100. The wearable apparatus for patient tracking 100 comprises a Bluetooth Low Energy module 116, button 102, a conductive loop 108, a wrist band 110, a BLE Beacon 112, an ID card pocket 120, a battery circuit board 118 and a battery 114.

The Bluetooth Low Energy module 116 comprises an button 102, a processor 104, an LED 122, and an antenna 106. Most patient tracking tags currently in-use are bulky and need the battery to be recharged or replaced. Utilizing BLE with a flexible circuit board allows for a strong thin, disposable plastic band to be used while keeping a low form factor for the electronic portion, and allowing it to be reusable.

A nurse may use the button 102 to activate the device which transmits to a BLE Beacon 112 which can receive location data for the patient. The wrist band 110 may also hold a name tag, in the ID card pocket 120, like conventional patient wrist bands.

A flexible, conductive loop 108 is used to detect tampering or removal of the wrist band 110 by detecting circuit continuity: a break in the conductive loop 108 would indicate tampering or removal. When removal or tampering is detected, the wrist band 110 could send a signal to the BLE Beacon 112 via processor 104 and the antenna 106.

The battery 114 may be on a circuit board, or may be placed on a separate board than the processor 104 and button 102 for added strength. After use, the wrist band 110 may be disposed, the battery 114 replaced, and then the electronic portions may be recycled. This allows for a low cost as well as a high degree of cleanliness, which is imperative in a medical facility. The button 102 may be used to control the power from the battery 114 to the Bluetooth Low Energy module 116, and the LED 122 may be used to indicate the state of the Bluetooth Low Energy module 116, allowing the user to see when the device is pairing, is low on power, etc.

Mesh Network Connectivity

Figure 2:
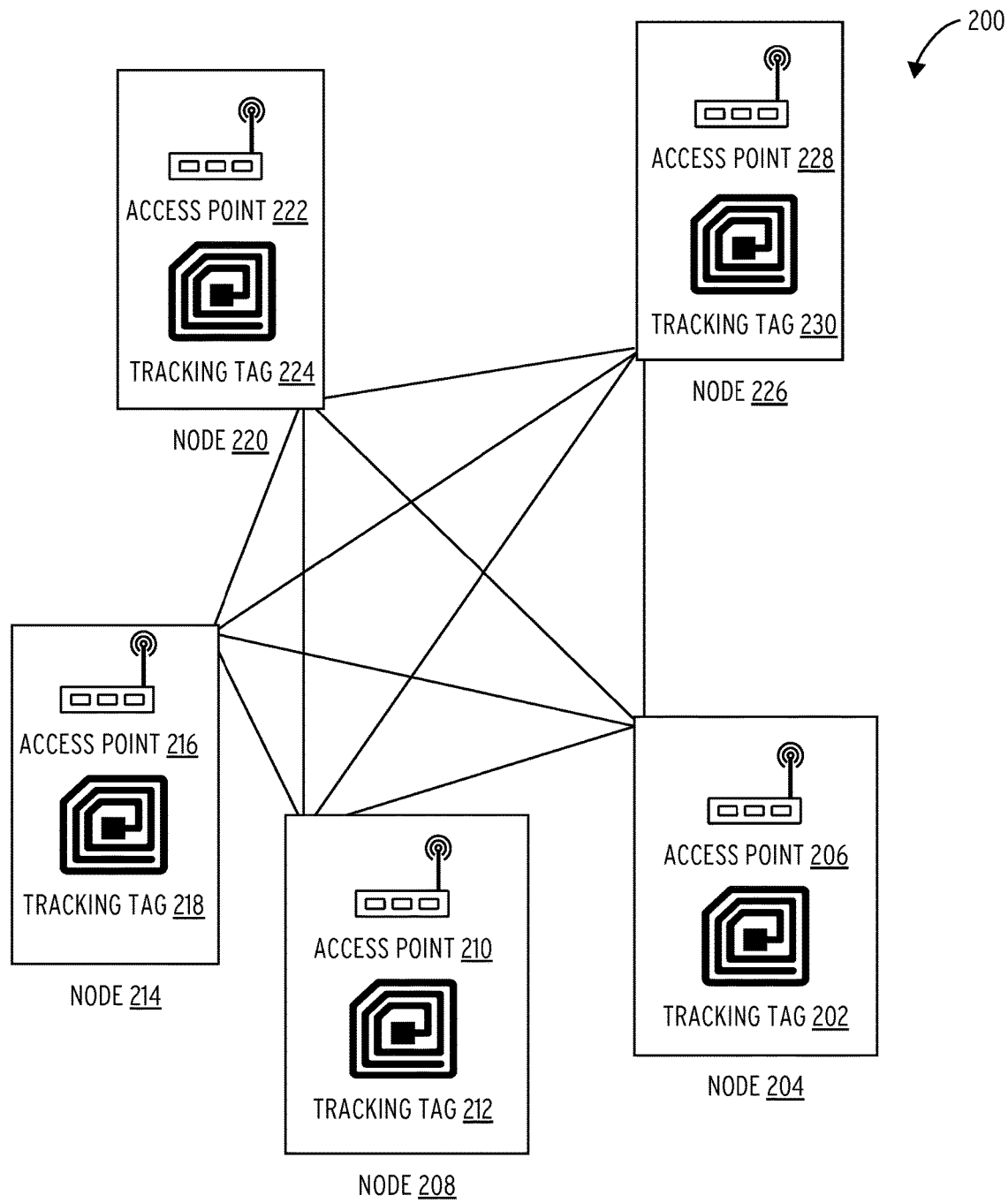
FIG. 2 illustrates an embodiment of a mesh network environment 200.

FIG. 2 illustrates an embodiment of a system 200 for integrating building automation infrastructure with location awareness utilizing wireless mesh technology. The system 200 may be operated in accordance with the process 300. The system 200 comprises the node 220, the node 226, the node 204, the node 214, the node 208.

The node 220 comprises the tracking tag 224, and the access point 222. The node 226 comprises the access point 228 and the tracking tag 230. The node 204 comprises the tracking tag 202 and the access point 206. The node 208 comprises the access point 210 and the tracking tag 212. The node 214 comprises the access point 216 and the tracking tag 218.

The system 200 may be established on an existing patient tracking network, with each node within the network having an access point and a tracking tag. The high density of access points for assets allows tracking of nodes and tags to be more accurate.

The system 200 is vendor agnostic and utilizes building automation infrastructure to track assets within a building. In addition, smart phones can be used with beacons to locate themselves within the building. The devices may now act as access points for beacon data in conjunction with one-another allowing smartphones, assets, and devices all to be located with respect to one-another.

In order to be tracked and located, each "dumb" appliance in a facility just needs a tag or module for the asset to be identifiable as a network node.

The nodes may be loaded with preset logic to activate a specific action on the "dumb" appliance it is attached to if a certain event occurs. For instance, if the appliance is carried outside of a designated area the node can tell the devices to sound an alarm.

This allows for integration with access control and surveillance which may greatly increase the efficiency of these systems by allowing for event-based tracking and alerts so that events may be prioritized and security may get automatically generated alerts, which is important for applications which are very sensitive to response time. This real-time location monitoring is also very useful for workflow optimization and monitoring as well as asset tracking to reduce lost inventory or un-locatable items.

The access point 206 receives the location of tracking tag 202 and transmits it to the tracking tag 224, the node 220 the tracking tag 218 and the tracking tag 212.

Tag Operation

Figure 3:
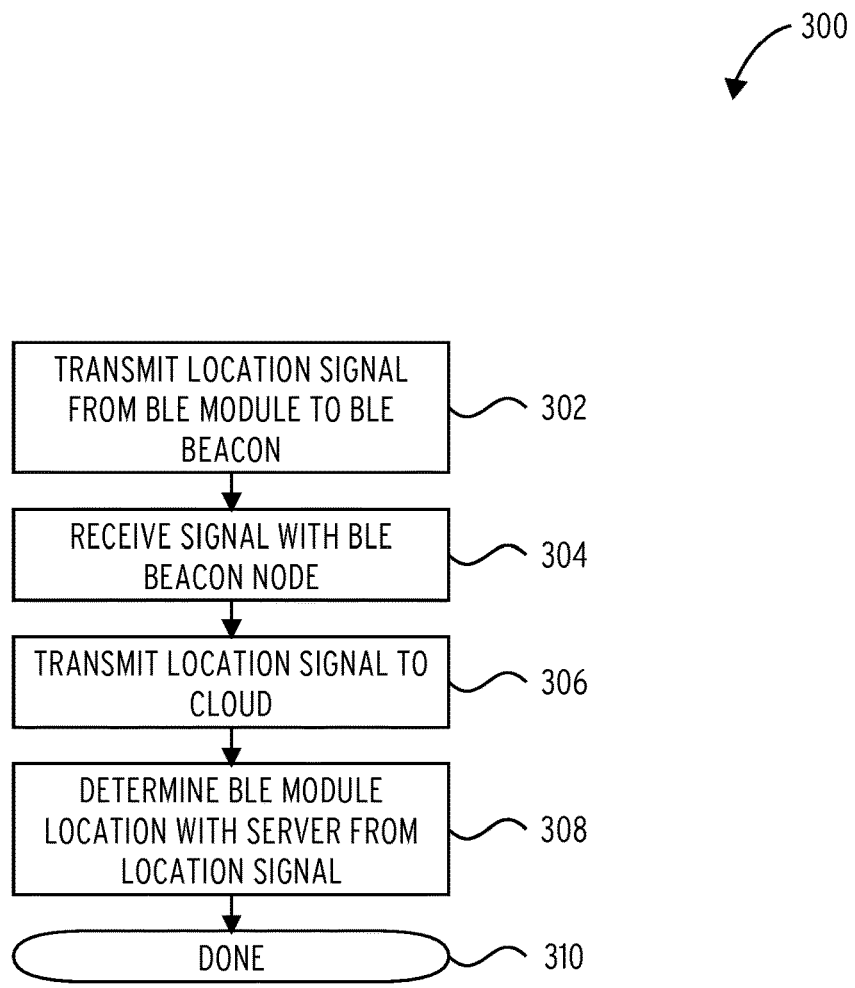
FIG. 3 illustrates a process for operating a wearable apparatus for patient tracking 300

FIG. 3 illustrates a process for operating a wearable apparatus for patient tracking 300. In block 302, the process 300 transmits a location signal from a BLE module to a BLE beacon. In block 304, the process 300 receives the signal with a BLE beacon node. In block 306, the process 300 transmits the location signal to the cloud. In block 308, the process 300 determines BLE module location with a server from location signal. In done block 310, the process 300 ends.

Figure 4:
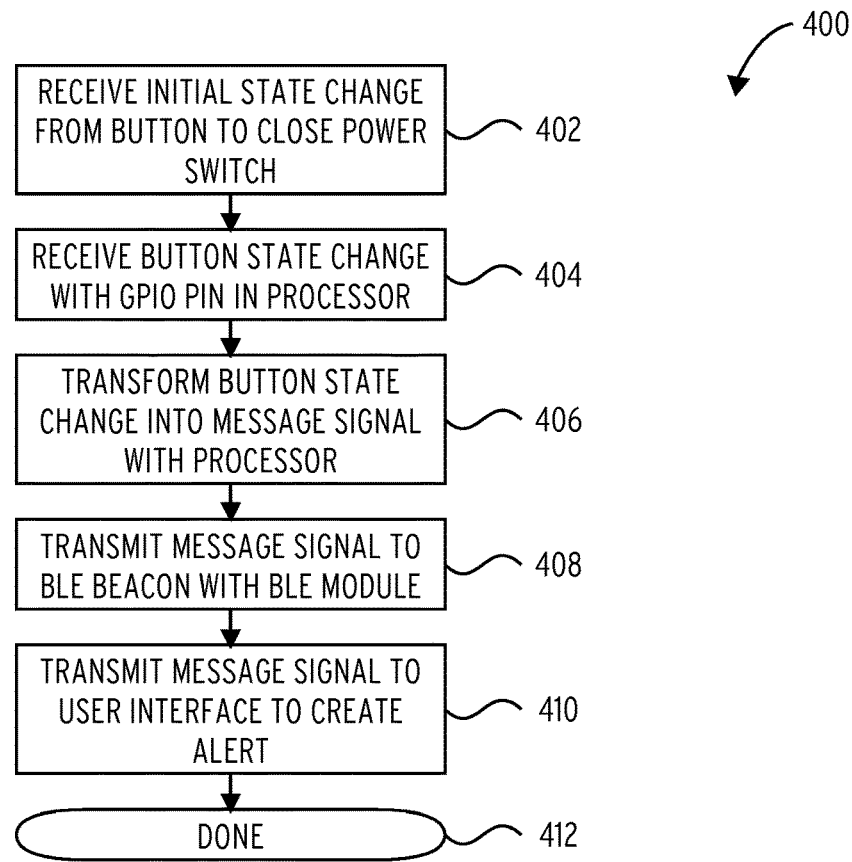
FIG. 4 illustrates a the process 400.
Figure 5:
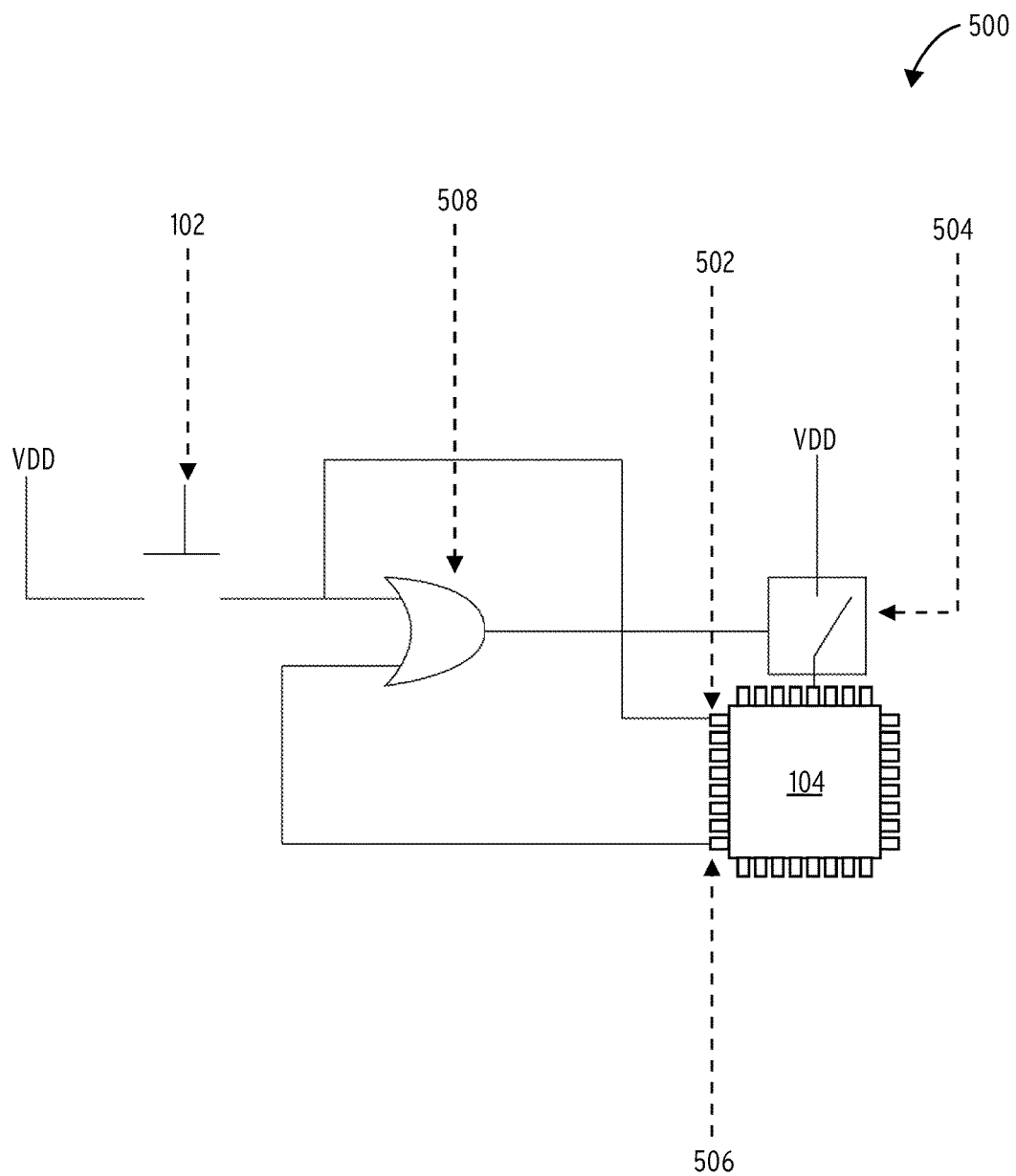
FIG. 5 illustrates an embodiment of a module power circuit 500.

FIG. 4 illustrates the process for controlling the state of a wearable apparatus for patient tracking 400. In block 402, the process 400 receives an initial state change from a button to close a power switch. In block 404, the process 400 receives a button state change with a GPIO pin in a processor. In block 406, the process 400 transforms the button state change into a message signal with the processor. In block 408, the process 400 transmits the message signal to a BLE beacon with a BLE module. In block 410, the process 400 transmits the message signal to a user interface to create an alert. In done block 412, the process 400 ends.

Tag Circuitry

The module power circuit 500 comprises a button 102, a processor 104, a GPIO pin 502, a switch 504, a GPIO pin 506, and a "or" logic circuit 508. The processor 104 and the button 102 are connected to the battery 114 via the button 102 with the processor 104 via its GPIO pins. This allows the Bluetooth Low Energy module 116 to remain offline until the button 102 is pressed and then the processor 104 may regulate the power to the circuit board. The GPIO pin 502 may be programmed to sense a change in the state of the button 102 so that the button 102 may be programmed to control functionality of the Bluetooth Low Energy module 116. By way of example, after the button 102 is used to turn on the Bluetooth Low Energy module 116, the processor 104 utilizes the GPIO pin 506 to keep the switch 504 closed and monitors the button state via the GPIO pin 502. When the button 102 is depressed for more than a certain number of seconds, the processor 104 may transmit a command to the BLE Beacon 112. This may be used to pair the Bluetooth Low Energy module 116 or may be programmed to indicate an emergency.

Tag as a Node in a Mesh Network

Figure 6:
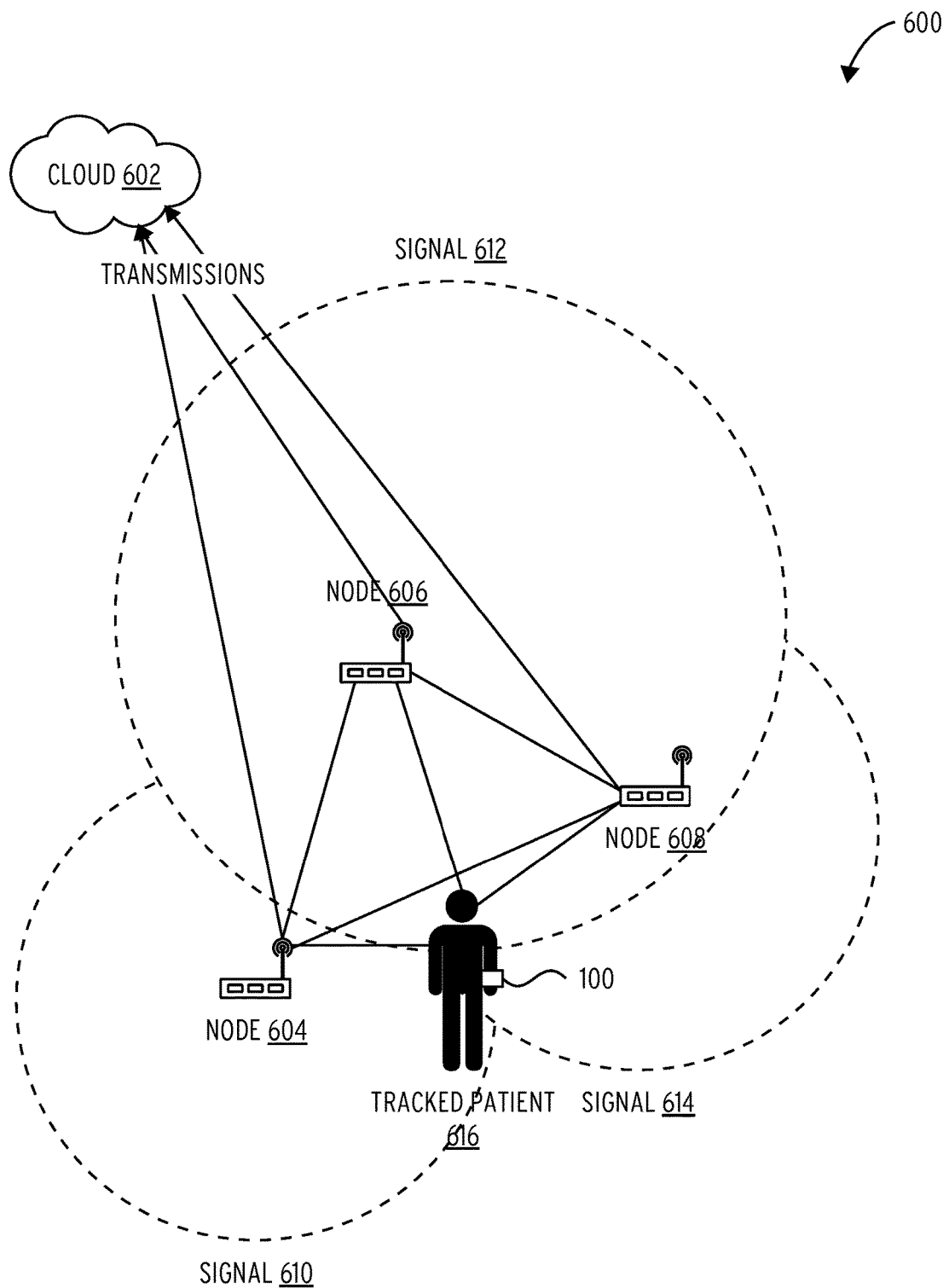
FIG. 6 illustrates an embodiment of a disposable patient tracking tag 600.

FIG. 6 illustrates an embodiment of a disposable patient tracking tag 600. The disposable patient tracking tag 600 comprises a wearable apparatus for patient tracking 100, a node 604, a node 606, a node 608, a signal 610, a signal 612, a signal 614, and a tracked patient 616.

The tracked patient 616 travels within range of node 606, node 604, and node 608 and receives and transmits signal 612, signal 614 and signal 610. The node 606, the node 608, the node 604 transmit data on the location and status of the wearable apparatus for patient tracking 100 and the associated tracked patient 616.

Hardware

Figure 7:
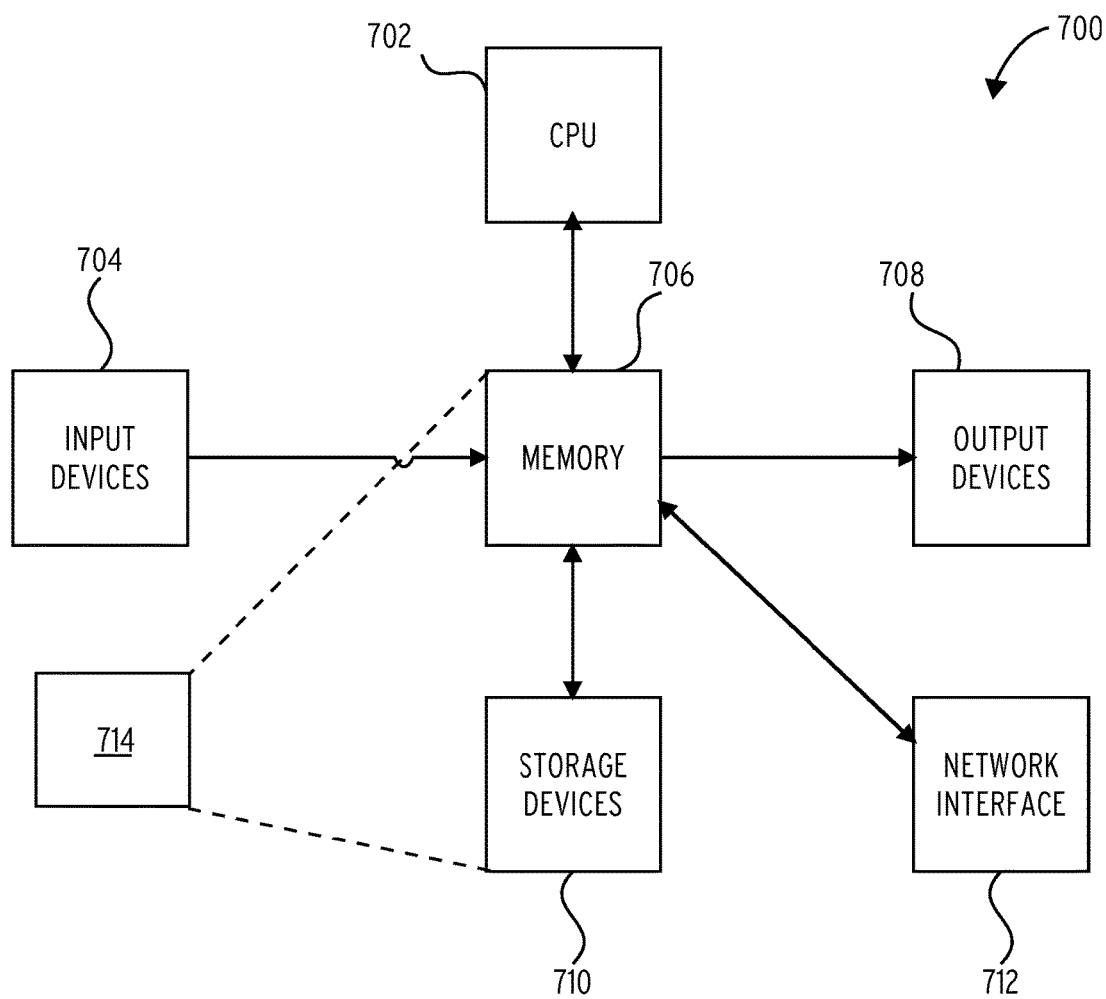
FIG. 7 illustrates an embodiment of a digital apparatus 700 to implement components and process steps of the system described herein.

FIG. 7 illustrates an embodiment of a digital apparatus 700 to implement components and process steps of the system described herein.

Input devices 704 comprise transducers that convert physical phenomenon into machine internal signals, typically electrical, optical or magnetic signals. Signals may also be wireless in the form of electromagnetic radiation in the radio frequency (RF) range but also potentially in the infrared or optical range. Examples of input devices 704 are keyboards which respond to touch or physical pressure from an object or proximity of an object to a surface, mice which respond to motion through space or across a plane, microphones which convert vibrations in the medium (typically air) into device signals, scanners which convert optical patterns on two or three dimensional objects into device signals. The signals from the input devices 704 are provided via various machine signal conductors (e.g., busses or network interfaces) and circuits to memory 706.

The memory 706 is typically what is known as a first or second level memory device, providing for storage (via configuration of matter or states of matter) of signals received from the input devices 704, instructions and information for controlling operation of the CPU 702, and signals from storage devices 710.

The memory 706 and/or the storage devices 710 may store computer-executable instructions and thus forming logic 714 that when applied to and executed by the CPU 702 implement embodiments of the apparatuses and processes disclosed herein.

Information stored in the memory 706 is typically directly accessible to the CPU 702 of the device. Signals input to the device cause the reconfiguration of the internal material/energy state of the memory 706, creating in essence a new machine configuration, influencing the behavior of the digital apparatus 700 by affecting the behavior of the CPU 702 with control signals (instructions) and data provided in conjunction with the control signals.

Second or third level storage devices 710 may provide a slower but higher capacity machine memory capability. Examples of storage devices 710 are hard disks, optical disks, large capacity flash memories or other non-volatile memory technologies, and magnetic memories.

The CPU 702 may cause the configuration of the memory 706 to be altered by signals in storage devices 710. In other words, the CPU 702 may cause data and instructions to be read from storage devices 710 in the memory 706 from which may then influence the operations of CPU 702 as instructions and data signals, and from which it may also be provided to the output devices 708. The CPU 702 may alter the content of the memory 706 by signaling to a machine interface of memory 706 to alter the internal configuration, and then converted signals to the storage devices 710 to alter its material internal configuration. In other words, data and instructions may be backed up from memory 706, which is often volatile, to storage devices 710, which are often non-volatile.

Output devices 708 are transducers which convert signals received from the memory 706 into physical phenomenon such as vibrations in the air, or patterns of light on a machine display, or vibrations (i.e., haptic devices) or patterns of ink or other materials (i.e., printers and 3-D printers).

The network interface 712 receives signals from the memory 706 and converts them into electrical, optical, or wireless signals to other machines, typically via a machine network. The network interface 712 also receives signals from the machine network and converts them into electrical, optical, or wireless signals to the memory 706.

Those having skill in the art will appreciate that there are various logic implementations by which processes and/or systems described herein can be effected (e.g., hardware, software, or firmware), and that the preferred vehicle will vary with the context in which the processes are deployed. If an implementer determines that speed and accuracy are paramount, the implementer may opt for a hardware or firmware implementation; alternatively, if flexibility is paramount, the implementer may opt for a solely software implementation; or, yet again alternatively, the implementer may opt for some combination of hardware, software, or firmware. Hence, there are numerous possible implementations by which the processes described herein may be effected, none of which is inherently superior to the other in that any vehicle to be utilized is a choice dependent upon the context in which the implementation will be deployed and the specific concerns (e.g., speed, flexibility, or predictability) of the implementer, any of which may vary. Those skilled in the art will recognize that optical aspects of implementations may involve optically-oriented hardware, software, and or firmware.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein. The techniques and procedures described herein may be implemented via logic distributed in one or more computing devices. The particular distribution and choice of logic will vary according to implementation.

The foregoing detailed description has set forth various embodiments of the devices or processes via the use of block diagrams, flowcharts, or examples. Insofar as such block diagrams, flowcharts, or examples contain one or more functions or operations, it will be understood as notorious by those within the art that each function or operation within such block diagrams, flowcharts, or examples can be implemented, individually or collectively, by a wide range of hardware, software, firmware, or virtually any combination thereof. Portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more processing devices (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually or collectively, by a wide range of hardware, software, firmware, or any combination thereof can be viewed as being composed of various types of circuitry.

Those skilled in the art will recognize that it is common within the art to describe devices or processes in the fashion set forth herein, and thereafter use standard engineering practices to integrate such described devices or processes into larger systems. At least a portion of the devices or processes described herein can be integrated into a network processing system via a reasonable amount of experimentation. Various embodiments are described herein and presented by way of example and not limitation.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Definitions

Various terminology is utilized herein, and should be assigned its conventional meaning in the relevant arts unless expressly defined herein.

"Building automation infrastructure" in this context refers technology and systems that aid the task of automatically locating, tracking, and managing patients and other assets within a hospital, medical office, or similar caregiving setting. This may include access points, routers, mobile devices, computer terminals, building wiring, sensors, actuators, and general network connectivity.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Programmable device" in this context refers to an integrated circuit designed to be configured and/or reconfigured after manufacturing. The term "programmable processor" is another name for a programmable device herein. Programmable devices may include programmable processors, such as field programmable gate arrays (FPGAs), configurable hardware logic (CHL), and/or any other type programmable devices. Configuration of the programmable device is generally specified using a computer code or data such as a hardware description language (HDL), such as for example Verilog, VHDL, or the like. A programmable device may include an array of programmable logic blocks and a hierarchy of reconfigurable interconnects that allow the programmable logic blocks to be coupled to each other according to the descriptions in the HDL code. Each of the programmable logic blocks may be configured to perform complex combinational functions, or merely simple logic gates, such as AND, and XOR logic blocks. In most FPGAs, logic blocks also include memory elements, which may be simple latches, flip-flops, hereinafter also referred to as "flops," or more complex blocks of memory. Depending on the length of the interconnections between different logic blocks, signals may arrive at input terminals of the logic blocks at different times.

"Software" in this context refers to logic implemented as processor-executable instructions in a machine memory (e.g. read/write volatile or nonvolatile memory or media).

Wireless Protocols

The system embodiments disclosed herein may utilize a variety of wireless communication technologies, including but not limited to the following:

"6LowPAN" in this context refers to an acronym of IPv6 (Internet Protocol Version 6) over Low power Wireless Personal Area Networks. It is a wireless standard for low-power radio communication applications that need wireless internet connectivity at lower data rates for devices with limited form factor. 6LoWPAN utilizes the RFC6282 standard for header compression and fragmentation. This protocol is used over a variety of networking media including Bluetooth Smart (2.4 GHz) or ZigBee or low-power RF (sub-1 GHz) and as such, the data rates and range may differ based on what networking media is used.

"Bluetooth Low-Energy (BLE)—or Bluetooth Smart" in this context refers to a wireless personal area network technology aimed at reduced power consumption and cost while maintaining a similar communication range as traditional Bluetooth. Like traditional Bluetooth, the frequency utilized is 2.4 GHz (ISM-Industrial, Scientific and Medical), the maximum range is generally 50-150 m with data rates up to 1 Mbps.

"Cellular" in this context refers to a communication network where the last link is wireless. The network is distributed over land areas called cells and utilizes one of the following standards GSM/GPRS/EDGE (2G), UMTS/HSPA (3G), LTE (4G). Frequencies are generally one of 900/1800/1900/2100 MHz. Ranges are 35 km max for GSM; 200 km max for HSPA and typical data download rates are: 35-170 kps (GPRS), 120-384 kbps (EDGE), 384 Kbps-2 Mbps (UMTS), 600 kbps-10 Mbps (HSPA), 3-10 Mbps (LTE).

"LoRaWAN" in this context refers to Low Power Wide Area Network, a media access control (MAC) protocol for wide area networks for low-cost, low-power, mobile, and secure bi-directional communication for large networks of up to millions of devices. LoRaWAN is employed on various frequencies, with a range of approximately 2-5 km (urban environment) to 15 km (suburban environment) and data rates of 0.3-50 kbps.

"NFC" in this context refers to "Near Field Communication" and is a subset of RFID (Radio Frequency Identifier) technology. NFC is standardized in ECMA-340 and ISO/IEC 18092. It employs electromagnetic induction between two loop antennae when NFC devices are within range (10 cm). NFC utilizes the frequency of 13.56 MHz (ISM). Data rates range from 106 to 424 kbit/s.

"SigFox" in this context refers to a cellular-style system that enables remote devices to connect using ultra-narrow band (UNB) technology and binary phase-shift keying (BPSK) to encode data. Utilizes the 900 MHz frequency and has a range of 30-50 km in rural environments and 3-10 km in urban environments with data rates from 10-1000 bps.

"Thread" in this context refers to a wireless mesh network standard that utilizes IEEE802.15.4 for the MAC (Media Access Control) and Physical layers, IETF IPv6 and 6LoW-PAN (IVP6). Thread operates at 250 kbps in the 2.4 GHz band. The IEEE 802.15.4-2006 version of the specification is used for the Thread stack.

"Weightless" in this context refers to an open machine to machine protocol which spans the physical and mac layers. Operating frequency: 200 MHz to 1 GHz (900 MHz (ISM) 470-790 MHz (White Space)) Fractional bandwidth of spectrum band: <8% (for continuous tuning). Range up to 10 km and data Rates which range from a few bps up to 100 kbps "WiFi" in this context refers to a wireless network standard based on 802.11 family which consists of a series of half-duplex over-the-air modulation techniques that use the same basic protocol. Frequencies utilized include 2.4 GHz and 5 GHz bands with a range of approximately 50 m. Data rate of 600 Mbps maximum, but 150-200 Mbps is more typical, depending on channel frequency used and number of antennas (latest 802.11-ac standard should offer 500 Mbps to 1 Gbps).

"Z-Wave" in this context refers to a wireless standard for reliable, low-latency transmission of small data packets. The Z-Wave utilizes the Z-Wave Alliance ZAD12837/ITU-T G.9959 standards and operated over the 900 MHz frequency in the US (Part 15 unlicensed ISM) and is modulated by Manchester channel encoding. Z-Wave has a range of 30 m and data rates up to 100 kbit/s.

"ZigBee" in this context refers to a wireless networking standard for low power, low data rate, and lost cost applications. The Zigbee protocol builds upon the Institute of Electrical and Electronics Engineers (IEEE) 802.15.4 standard which defines a short range, low power, low data rate wireless interface for small devices that have constrained power, CPU, and memory resources. Zigbee operates over the 2.4 GHz frequency, with a range of 10-100 m and data rates of 250 kbps.

What is claimed is:

1. An apparatus for tracking patients comprising:
   a PCB substrate, which is at least partially flexible, of a set length, further comprising:
      a low power wireless transceiver and microcontroller that is adapted to communicate with a network;
      a pushbutton;
      a battery; and
      circuitry to couple the same;
   a wearable band made of flexible material, further comprising of:
      an opening and enclosure that is at least as long as the set length of the PCB substrate;
      the PCB substrate formed for insertion into the opening of the wearable band and formed to secure inside the enclosure;
   the flexible material formed to enable the pushbutton on the PCB substrate to be pressed while secured inside the enclosure; and
   the wearable band configured to securely fasten to a patient.

2. The apparatus of claim 1 wherein the pushbutton is operable to toggle the wireless transceiver and microcontroller to power on and remain on for a set duration of time.

3. The apparatus of claim 1 wherein the pushbutton is operable to send a control signal to the wireless transceiver and microcontroller.

4. The apparatus of claim 1 wherein the PCB substrate is fully flexible.

5. The apparatus of claim 1 wherein the circuitry further comprises a tamper wire that runs along the set length of the PCB substrate.

6. The apparatus of claim 5 wherein the tamper wire is placed in a loop along the PCB substrate such that when a user removes the wearable band the tamper wire connection is broken and a circuit is opened.

7. The apparatus of claim 6 configured such that if the circuit is opened the wireless transceiver communicates to the network that a tag was removed from the patient.

8. The apparatus of claim 1 further comprising of a temperature sensor, the apparatus adapted such that if the temperature sensor's reading drops below a threshold the wireless transceiver communicates to the network that a tag was removed from the patient.

9. The apparatus of claim 1 wherein the wearable band further comprises of a slot for a nametag.

10. The apparatus of claim 1 wherein the wireless transceiver complies with the Bluetooth Low Energy standard.

11. The apparatus of claim 1 wherein the wireless transceiver and microcontroller are adapted to communicate to a mobile device to provide data to identify a tag.

12. The apparatus of claim 1 wherein the wireless transceiver and microcontroller are adapted to communicate to a mobile device to receive configuration settings.

* * * * *